United States Patent
Cotts et al.

(10) Patent No.: US 6,586,550 B2
(45) Date of Patent: Jul. 1, 2003

(54) POLYMERIZATION OF OLEFINS

(75) Inventors: Patricia Metzger Cotts, Wilmington, DE (US); William Howard Tuminello, Newark, DE (US); Lin Wang, Hockessin, DE (US); Joel David Citron, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/900,954

(22) Filed: Jul. 9, 2001

(65) Prior Publication Data

US 2002/0007034 A1 Jan. 17, 2002

Related U.S. Application Data

(63) Continuation of application No. 09/408,250, filed on Sep. 29, 1999, now Pat. No. 6,297,338, which is a continuation-in-part of application No. 09/273,409, filed on Mar. 22, 1999, now Pat. No. 6,214,761.
(60) Provisional application No. 60/117,471, filed on Jan. 27, 1999, and provisional application No. 60/080,018, filed on Mar. 30, 1998.

(51) Int. Cl.$^7$ ............................................. C08F 110/02
(52) U.S. Cl. ........................................................ 526/352
(58) Field of Search ........................................ 526/352

(56) References Cited

U.S. PATENT DOCUMENTS

| | | |
|---|---|---|
| 5,071,927 A | 12/1991 | Benham et al. |
| 5,137,994 A | 8/1992 | Goode et al. |
| 5,595,705 A | 1/1997 | Walton et al. |
| 5,686,542 A | 11/1997 | Ostoja-Starzewski et al. |
| 5,753,785 A | 5/1998 | Reddy et al. |
| 5,856,610 A | 1/1999 | Tamura et al. |

FOREIGN PATENT DOCUMENTS

| | | |
|---|---|---|
| EP | 0 361 363 A2 | 4/1990 |
| WO | WO 90/15085 A1 | 12/1990 |
| WO | WO 96/23010 A2 | 8/1996 |
| WO | WO 9623010 * | 8/1996 |
| WO | WO 98/27124 A1 | 6/1998 |
| WO | WO 99/02472 A1 | 1/1999 |
| WO | WO 99/12981 A1 | 3/1999 |

OTHER PUBLICATIONS

Benham, E .A. et al., A Process for the Simultaneious Oligomerization and Copolymerization of Ethylene, Polymer Engineering and Science, Nov., 1998, pp. 1469–1472, 28(22).

Denger, C. et al., Simultaneous oligomerization and polymerization of ethylene, Makromol. Chem., Rapid Commun., 1991, pp. 697–701, 12.

Barnhart, R. W. et al., Synethesis of Branched Polyolefins Using a Combination of Homogeneous Metallocene Mimics, J. Am. Chem. Soc., 1998, pp. 1082–1083, 120.

Copy of International Search Report dated Aug. 24, 1999.

* cited by examiner

*Primary Examiner*—David W. Wu
*Assistant Examiner*—William Cheung

(57) ABSTRACT

Polyolefins made preferably only from ethylene using a selected ethylene oligomerization catalyst to form α-olefins and a polymerization catalyst which can copolymerize ethylene and α-olefins produces a novel polymer which advantageous rheological properties.

22 Claims, 2 Drawing Sheets

POLYMERIZATION OF OLEFINS

This application is a continuation of application Ser. No. 09/408,250, filed Sep. 29, 1999, now U.S. Pat. No. 6,297,338 which is a continuation-in-part of application Ser. No. 09/273,409, filed Mar. 22, 1999, now U.S. Pat. No. 6,214,761, and which further claims priority under 35 U.S.C. §119(e) from provisional application Ser. Nos. 60/117,471, filed Jan. 27, 1999, and 60/080,018, filed Mar. 30, 1998.

FIELD OF THE INVENTION

Polymers with varied and useful properties may be produced in processes using at least two polymerization catalysts, at least one of which is a selected iron or cobalt catalyst, for the synthesis of polyolefins. Novel polymers with improved properties are made using a selected ethylene oligomerization catalyst to form α-olefins and a polymerization catalyst capable of copolymerizing ethylene and α-olefins.

TECHNICAL BACKGROUND

Polyolefins are most often prepared by polymerization processes in which a transition metal containing catalyst system is used. Depending on the process conditions used and the catalyst system chosen, polymers, even those made from the same monomer(s) may have varying properties. Some of the properties which may change are molecular weight and molecular weight distribution, crystallinity, melting point, branching, and glass transition temperature. Except for molecular weight and molecular weight distribution, branching can affect all the other properties mentioned.

It is known that certain transition metal containing polymerization catalysts containing iron or cobalt, are especially useful in polymerizing ethylene and propylene, see for instance U.S. patent applications Ser. No. 08/991,372, filed Dec. 16, 1997, now U.S. Pat. No. 5,455,555 and Ser. No. 09/006,031, filed Jan. 12, 1998 now U.S. Pat. No. 6,150,482 ("equivalents" of World Patent Applications 98/27124 and 98/30612). It is also known that blends of distinct polymers, that vary for instance in molecular weight, molecular weight distribution, crystallinity, and/or branching, may have advantageous properties compared to "single" polymers. For instance it is known that polymers with broad or bimodal molecular weight distributions may often be melt processed (be shaped) more easily than narrower molecular weight distribution polymers. Also, thermoplastics such as crystalline polymers may often be toughened by blending with elastomeric polymers.

Therefore, methods of producing polymers which inherently produce polymer blends are useful especially if a later separate (and expensive) polymer mixing step can be avoided. However in such polymerizations one should be aware that two different catalysts may interfere with one another, or interact in such a way as to give a single polymer.

Various reports of "simultaneous" oligomerization and polymerization of ethylene to form (in most cases) branched polyethylenes have appeared in the literature, see for instance World Patent Application 90/15085, U.S. Pat. Nos. 5,753,785, 5,856,610, 5,686,542, 5,137,994, and 5,071,927, C. Denger, et al,. Makromol. Chem. Rapid Commun., vol. 12, p. 697–701 (1991), and E. A. Benham, et al., Polymer Engineering and Science, vol. 28, p. 1469–1472 (1988). None of these references specifically describes any of the processes herein or any of the branched homopolyethylenes claimed herein.

SUMMARY OF THE INVENTION

This invention concerns a polyethylene which has one or both of a structural index, $S_T$, of about 1.4 or more, and a processability index, $P_R$ of about 40 or more, provided that if $S_T$ is less than about 1.4, said polymer has fewer than 20 methyl branches per 1000 methylene groups.

This invention also concerns a polyethylene which has at least 2 branches each of ethyl and n-hexyl or longer and at least one n-butyl per 1000 methylene groups, and has fewer than 20 methyl branches per 1000 methylene groups, and obeys the equation $$[\eta] < 0.0007\, M_w^{0.63}$$

wherein $[\eta]$ is the intrinsic viscosity of said polyethylene in 1,2,4-trichlorbenzene at 150° C. and $M_w$ is the weight average molecular weight.

DETAILS OF THE INVENTION

Figure 1:
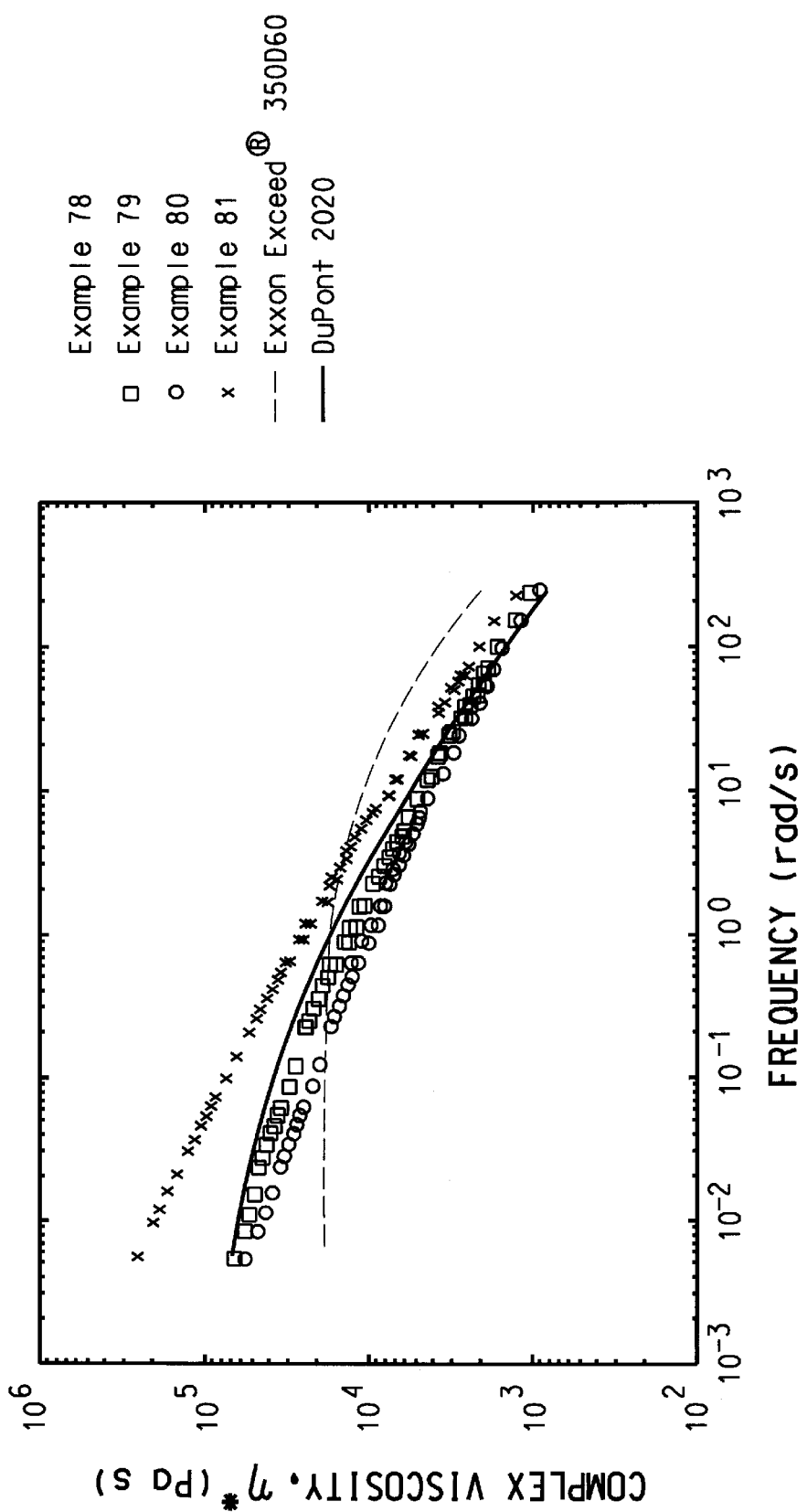
FIG. 1 shows the complex viscosity of polyethylenes, versus frequency of the rheometer, as described in Example 30.

In the polymerization processes and catalyst compositions described herein certain groups may be present. By hydrocarbyl is meant a univalent radical containing only carbon and hydrogen. By substituted hydrocarbyl herein is meant a hydrocarbyl group which contains one or more (types of) substitutents that does not interfere with the operation of the polymerization catalyst system. Suitable substituents in some polymerizations may include some or all of halo, ester, keto (oxo), amino, imino, carboxyl, phosphite, phosphonite, phosphine, phosphinite, thioether, amide, nitrile, and ether. Preferred substituents are halo, ester, amino, imino, carboxyl, phosphite, phosphonite, phosphine, phosphinite, thioether, and amide. Which substitutents are useful in which polymerizations may in some cases be determined by reference to U.S. patent application Ser. No. 08/991,372, filed Dec. 16, 1997, now U.S. Pat. No. 5,955,55 and 09/006,031, filed Jan. 12, 1998 now U.S. Pat. No. 6,150,482 (and their corresponding World Patent Applications), both of which are hereby included by reference. By an aryl moiety is meant a univalent group whose free valence is to a carbon atom of an aromatic ring. The aryl moiety may contain one or more aromatic ring and may be substituted by inert groups. By phenyl is meant the $C_6H_5$-radical, and a phenyl moiety or substituted phenyl is a radical in which one or more of the hydrogen atoms is replaced by a substituent group (which may include hydrocarbyl). Preferred substituents for substituted phenyl include those listed above for substituted hydrocarbyl, plus hydrocarbyl. If not otherwise stated, hydrocarbyl, substituted hydrocarbyl and all other groups containing carbon atoms, such as alkyl, preferably contain 1 to 20 carbon atoms.

By a polymerization catalyst activator is meant a compound that reacts with a transition metal compound to form an active polymerization catalyst. A preferred polymerization catalyst activator is an alkylaluminum compound, that is a compound which has one or more alkyl groups bound to an aluminum atom.

By a polymerization catalyst component is meant a composition that by itself, or after reaction with one or more other compounds (optionally in the presence of the olefins to be polymerized), catalyzes the polymerization of olefins.

Noncoordinating ions are mentioned and useful herein. Such anions are well known to the artisan, see for instance W. Beck., et al., Chem. Rev., vol. 88, p. 1405–1421 (1988), and S. H. Strauss, Chem. Rev., vol. 93, p. 927–942 (1993), both of which are hereby included by reference. Relative coordinating abilities of such noncoordinating anions are described in these references, Beck at p. 1411, and Strauss at p. 932, Table III. Useful noncoordinating anions include $SbF_6^-$, BAF, $PF_6^-$, or $BF_4^-$, wherein BAF is tetrakis[3,5-bis(trifluoromethyl)phenyl]borate.

A neutral Lewis acid or a cationic Lewis or Bronsted acid whose counterion is a weakly coordinating anion is also present as part of the catalyst system. By a "neutral Lewis acid" is meant a compound which is a Lewis acid capable of abstracting X from (II) to form a weakly coordination anion.

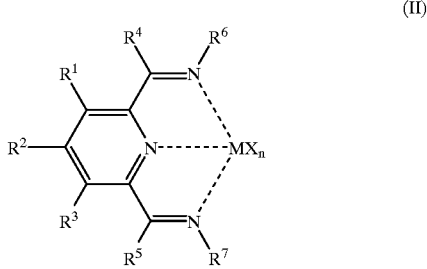

(II)

In (II), M is Co or Fe, each X is independently and anion and each X is such that the total negative charges on X equal the oxidation state of M. The neutral Lewis acid is originally uncharged (i.e., not ionic). Suitable neutral Lewis acids include $SbF_5$, $Ar_3B$ (wherein Ar is aryl), and $BF_3$. By a cationic Lewis acid is meant a cation with a positive charge such as $Ag^+$, $H^+$, and $Na^+$.

In those instances in which (II) does not contain an alkyl or hydride group already bonded to the metal (i.e., X is not alkyl or hydride), the neutral Lewis acid or a cationic Lewis or Bronsted acid also alkylates or adds a hydride to the metal, i.e., causes an alkyl group or hydride to become bonded to the metal atom, or a separate compound is added to add the alkyl or hydride group.

A preferred neutral Lewis acid, which can alkylate the metal, is a selected alkyl aluminum compound, such as $R^9{}_3Al$, $R^9{}_2AlCl$, $R^9AlC_2$, and "$R^9AlO$" (alkylaluminoxanes), wherein $R^9$ is alkyl containing 1 to 25 carbon atoms, preferably 1 to 4 carbon atoms. Suitable alkyl aluminum compounds include methylaluminoxane (which is an oligomer with the general formula $[MeAlO]_n$), $(C_2H_5)_2AlCl$, $C_2H_5AlCl_2$, and $[(CH_3)_2CHCH_2]_3Al$ Metal hydrides such as $NaBH_4$ may be used to bond hydride groups to the metal M.

For (I) and (II) preferred formulas and compounds are found in U.S. patent application Ser. No. 08/991,372, filed Dec. 16, 1997, now U.S. Pat. No. 5,955,555 and Ser. No. 09/006,031, filed Jan. 12, 1998, U.S. Pat. No. 6,150,482 and preferred groupings and compounds in these applications are also preferred herein. However the compound numbers and group (i.e., $R^x$) numbers in these applications may vary from those herein, but they are readily convertible. These applications also describe synthesis of (I) and (II).

There are many different ways of preparing active polymerization catalysts from (I) or (II) many of which are described in U.S. patent application Ser. No. 08/991,372, filed Dec. 16, 1997, U.S. Pat. No. 5,955,555 and Ser. No. 09/006,031, filed Jan. 12, 1998, U.S. Pat. No. 6,150,482 and those so described are applicable herein. "Pure" compounds which themselves may be active polymerization catalysts may be used, or the active polymerization catalyst may be prepared in situ by a variety of methods.

For instance, olefins may be polymerized by contacting, at a temperature of about −100° C. to about +200° C. a first compound W, which is a neutral Lewis acid capable of abstracting $X^-$ to form $WX^-$, provided that the anion formed is a weakly coordinating anion; or a cationic Lewis or Bronsted acid whose counterion is a weakly coordinating anion.

Which first active polymerization catalysts will polymerize which olefins, and under what conditions, will also be found in U.S. patent application Ser. No. 08/991,372, filed Dec. 16, 1997, U.S. Pat. No. 5,955,555 and Ser. No. 09/006,031, filed Jan. 12, 1998 U.S. Pat. No. 6,150,482. Monomers useful herein for the first active polymerization catalyst include ethylene and propylene. A preferred monomer for this catalyst is ethylene.

In one preferred process described herein the first and second olefins are identical, and preferred olefins in such a process are the same as described immediately above. The first and/or second olefins may also be a single olefin or a mixture of olefins to make a copolymer. Again it is preferred that they be identical, particularly in a process in which polymerization by the first and second polymerization catalysts make polymer simultaneously.

In some processes herein the first active polymerization catalyst may polymerize a monomer that may not be polymerized by said second active polymerization catalyst, and/or vice versa. In that instance two chemically distinct polymers may be produced. In another scenario two monomers would be present, with one polymerization catalyst producing a copolymer, and the other polymerization catalyst producing a homopolymer, or two copolymers may be produced which vary in the molar proportion or repeat units from the various monomers. Other analogous combinations will be evident to the artisan.

In another variation of the process described herein one of the polymerization catalysts makes an oligomer of an olefin, preferably ethylene, which oligomer has the formula $R^{60}CH=CH_2$, wherein $R^{60}$ is n-alkyl, preferably with an even number of carbon atoms. The other polymerization catalyst in the process (co)polymerizes this olefin, either by itself or preferably with at least one other olefin, preferably ethylene, to form a branched polyolefin. Preparation of the oligomer (which is sometimes called an α-olefin) by a first active polymerization-type of catalyst can be found in U.S. patent application Ser. No. 09/005,965, filed Jan. 12, 1998 U.S. Pat. No. 6,111,004 ("equivalent" of World Patent Application 99/02472), and B. L. Small, et. al., J. Am. Chem. Soc., vol. 120, p. 7143–7144 (1998), all of which are hereby included by reference. These references describe the use of a limited class of compounds such as (II) to prepare compounds of the formula $R^{60}CH=CH_2$ from ethylene, and so would qualify as a catalyst that produces this olefin. In a preferred version of this process one of these first-type polymerization is used to form the α-olefin, and the second active polymerization catalyst is a catalyst which is capable of copolymerizing ethylene and olefins of the formula $R^{60}CH=CH_2$, such as a Ziegler-Natta-type or metallocene-type catalyst. Other types of such catalysts include transition metal complexes of amidimidates and certain iron or cobalt complexes of (I). The amount of branching due to incorporation of the olefin $R^{60}CH=CH_2$ in the polymer can be controlled by the ratio of α-olefin forming polymerization catalyst to higher polymer forming olefin polymerization catalyst. The higher the proportion of α-olefin forming polymerization catalyst the higher the amount of branching. The homopolyethylenes that are made may range from polymers with little branching to polymers which contain many branches, that is from highly crystalline to amorphous homopolyethylenes. In one preferred form, especially when a crystalline polyethylene is being made, the process is carried out in the gas phase. It is believed that in many cases in gas phase polymerization when both catalysts are present in the same particle on which polymerization is taking place (for example originally a supported catalyst), the α-olefin is especially efficiently used (polymerized into the resulting polymer). When amorphous or only slightly crystalline homopolyethylenes are being made the process may be carried out in liquid slurry or solution.

In the variation of the process described in the immediately preceding paragraph a novel homopolyethylene is produced. By "homopolyethylene" in this instance is meant a polymer produced in a polymerization in which ethylene is the only polymerizable olefin added to the polymerization process in a single step, reactor, or by simultaneous reactions. However it is understood that the polymer produced is not made by the direct polymerization of ethylene alone, but by the copolymerization of ethylene and α-olefins which are produced in situ. The polymer produced usually contains only branches of the formula (excluding end groups) —$(CH_2CH_2)_nH$ wherein n is 1 or more, preferably 1 to 100, more preferably 1 to 30, of these branches per 1000 methylene atoms. Normally there will be branches with a range of "n" in the polymer. The amount of these branches (as measured by total methyl groups) in the polymer preferably ranges from about 2 to about 200, especially preferably about 5 to about 175, more preferably about 10 to about 150, and especially preferably about 20 to about 150 branches per 1000 methylene groups in the polymer (for the method of measurement and calculation, see World Patent Application 96/23010). Another preferable range for these branches is about 50 to about 200 methyl groups per 1000 methylene carbon atoms. It is also preferable (either alone or in combination with the other preferable features above) that in these branched polymers there is at least 2 branches each of ethyl and n-hexyl or longer and at least one n-butyl per 1000 methylene groups, more preferably at least 4 branches each of ethyl and n-hexyl or longer and at least 2 n-butyl branches per 1000 methylene groups, and especially preferably at least 10 branches each of ethyl and n-hexyl or longer and at least 5 n-butyl branches per 1000 methylene groups. It is also preferred that there are more ethyl branches than butyl branches in this homopolyethylene. In another preferred polymer (alone or in combination with any of the above preferred features) there is less than 20 methyl branches, more preferably less than 2 methyl branch, and especially preferably less than 2 methyl branches (all after correction for end groups) per 1000 methylene groups.

In the polymerizations to make the "homopolyethylene" only a single high molecular weight polymer is produced, that is a polymer which has an average degree of polymerization of at least 50, more preferably at least 200, and especially preferably at least 400. The synthesis of the branched homopolyethylene is believed to be successful in part because the catalyst which produces the α-olefin often does so at a rate comparable with the polymerization rate, both of them, for the sake of low cost, being relatively rapid.

These homopolyethylenes also have unusual properties, which gives them much better processability in processes in which high low shear viscosity and/or low high shear viscose is desirable. For instance, some of the polymers produced by the polymerization herein have unusual rheological properties that make them suitable for the uses described herein. Using the data shown in FIG. 1, one can calculate certain indices which reflect the improved processing properties. A structural index, $S_T$, which is defined as $$S_T = \eta_0/(8.33 \times 10^{-14})(M_w)^{3.4}$$

wherein $\eta_0$ is the zero shear viscosity at 140° C. and $M_w$ is the weight average molecular weight of the polymer. Materials that have a large proportion of carbon atoms in long chain branches as opposed to short chain branches will have a relatively high $S_T$. Preferably the polymer used herein have an $S_T$ of about 1.4 or more, more preferably about 2.0 or more. The $S_T$ of various polymers in the Examples is given in Table 12, at the end of Example 30.

Another index which may be used to measure the potential good processability of a polymer, based on its rheological properties, is $P_R$, the Processability Index. This is a shear thinning index, and is defined as $$P_R = (\eta^* \text{ at } 0.00628 \text{ rad/s})/(\eta^* \text{ at } 188 \text{ rad/s})$$

wherein $\eta^*$ is the viscosity at the indicated rate of the viscometer. This is similar to other ratios of vicosities at different shear levels, but covers a broader range of shears. The higher the value of $P_R$ the greater the shear thinning of the polymer. It is preferred that $P_R$ of the polymers used herein be about 40 or more, more preferably about 50 or more, and especially preferably about 100 or more. Furthermore, any combination of $S_T$ and $P_R$ values mentioned herein are also preferred.

Figure 2:
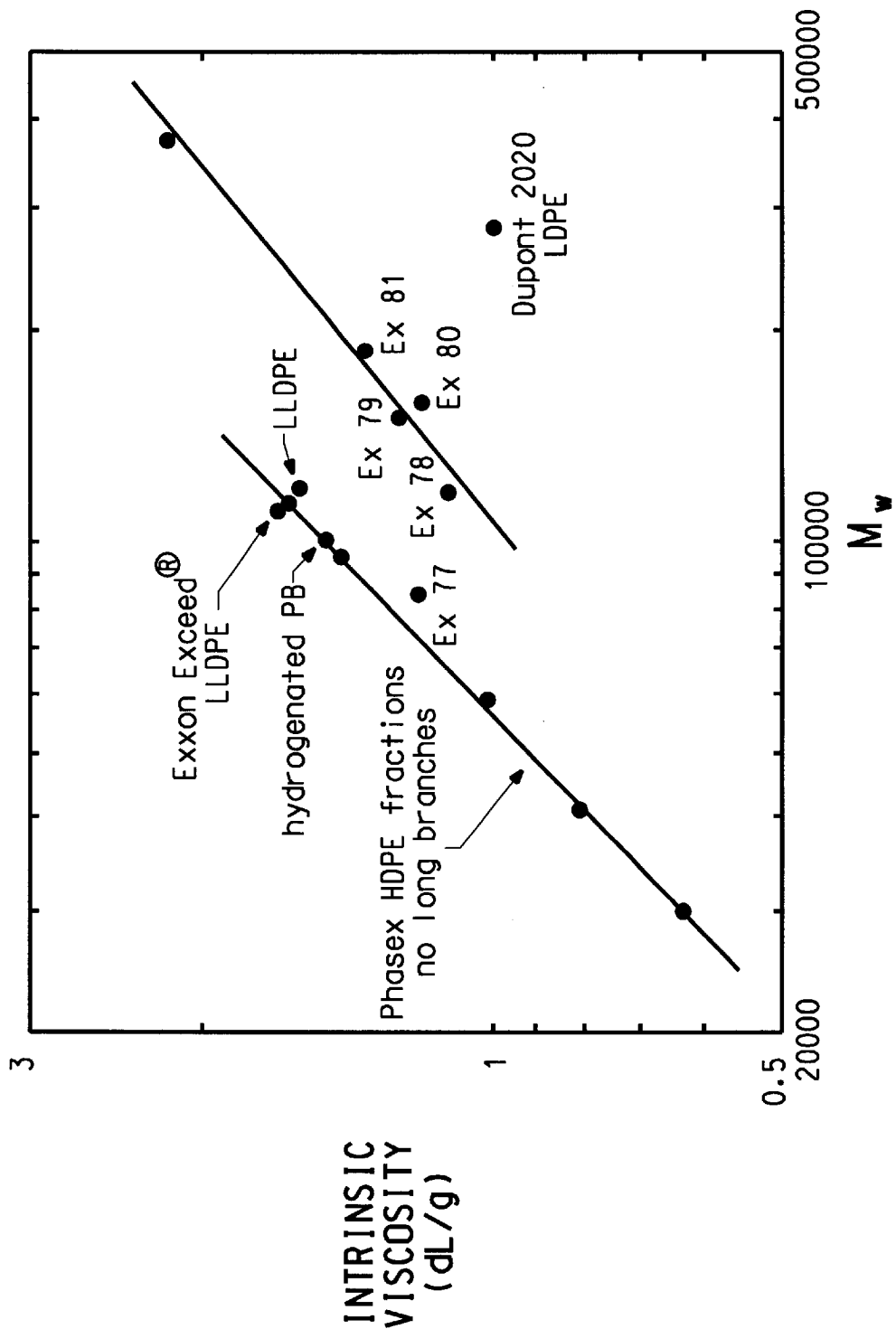
FIG. 2 shows the intrinsic viscosity, $[\eta]$, vs. the weight average molecular weight, Mw, for a series of polymers of this invention plus various other polymers, which are labeled.

Another way of finding polymers which may have good rheology (and possibly long chain branching) is the measuring the Mw versus the intrinsic viscosity. Polymers with good processing characteristics will have a lower intrinsic viscosity for a given Mw versus a (possibly more linear) worse processing polymer. FIG. 2 shows such relationships between various polyethylenes and other similar polymers, some of which are branched. It is clear that the polymers of this invention have lower intrinsic viscosities for their Mw's than similar "linear" polyethylenes. The line on the right is fitted to the present invention, while the line on the left is fitted to linear polyethylenes or polyethylenes with short chain branching only, such as typical LLDPEs such as Exxon's Exceed®. Indeed for the "better" polymers produced herein one could have the relationship $$[\eta] < 0.0007 \text{ Mw}^{0.66}$$

and it is preferred that $$[\eta] < 0.0007 \text{ Mw}^{0.63}$$

Of the two lines shown in FIG. 2, the left hand line is of the equation $$[\eta] = 0.00054 \text{ Mw}^{0.69}$$

while the right hand line is of the equation $$[\eta] = 0.00094 \text{ Mw}^{0.60}$$

For the purposes of these equations, Mw is determined by light scattering and intrinsic viscosity is determined in 1,2,4-trichlorobenzene at 150° C. (see below). The polymers of the present invention, especially when they have few methyl groups, and optionally one or more of the other branching patterns described above are thus novel.

Likewise, conditions for such polymerizations, particularly for catalysts of the first active polymerization type, will also be found in all of these patent applications. Briefly, the temperature at which the polymerization is carried out is about −100° C. to about +200° C., preferably about −20° C. to about +80° C. The polymerization pressure which is used with a gaseous olefin is not critical, atmospheric pressure to about 275 MPa, or more, being a suitable range. With a liquid monomer the monomer may be used neat or diluted with another liquid (solvent) for the monomer. The ratio of W:(I), when W is present, is preferably about 1 or more, more preferably about 10 or more when only W (no other Lewis acid catalyst) is present. These polymerizations may be batch, semi-batch or continuous processes, and may be carried out in liquid medium or the gas phase (assuming the monomers have the requisite volatility). These details will also be found in U.S. patent applications Ser. No. 08/991,372, filed Dec. 16, 1997, U.S. Pat. No. 5,955,555 and Ser. No. 09/006,031, filed Jan. 12, 1998, U.S. Pat. No. 6,150,482 and Ser. No. 09/005,965, filed Jan. 12, 1998.

In these polymerization processes preferred groups for $R^6$ is

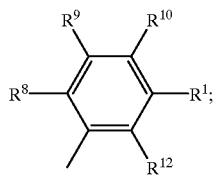
(III)

and for $R^7$ is

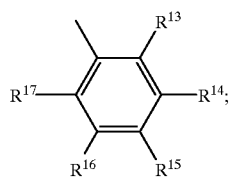
(IV)

wherein:
$R^8$ and $R^{13}$ are each independently hydrocarbyl, substituted hydrocarbyl or an inert functional group;
$R^9$, $R^{10}$, $R^{11}$, $R^{14}$, $R^{15}$ and $R^{16}$ are each independently hydrogen, hydrocarbyl, substituted hydrocarbyl or an inert functional group;
$R^{12}$ and $R^{17}$ are each independently hydrogen, hydrocarbyl, substituted hydrocarbyl or an inert functional group;
and provided that any two of $R^8$, $R^9$, $R^{10}$, $R^{11}$, $R^{12}$, $R^{13}$, $R^{14}$, $R^{15}$, $R^{16}$ and $R^{17}$ that are vicinal to one another, taken together may form a ring.

Two chemically different active polymerization catalysts are used in the polymerization described herein. The first active polymerization catalyst is described in detail above. The second active polymerization catalyst may also meet the limitations of the first active polymerization catalyst, but must be chemically distinct. For instance, it may have a different transition metal present, and/or utilize a ligand which differs in structure between the first and second active polymerization catalysts. In one preferred process, the ligand type and the metal are the same, but the ligands differ in their substituents.

Included within the definition of two active polymerization catalysts are systems in which a single polymerization catalyst is added together with another ligand, preferably the same type of ligand, which can displace the original ligand coordinated to the metal of the original active polymerization catalyst, to produce in situ two different polymerization catalysts.

However other types of catalysts may also be used for the second active polymerization catalyst. For instance so-called Ziegler-Natta and/or metallocene-type catalysts may also be used. These types of catalysts are well known in the polyolefin field, see for instance Angew. Chem., Int. Ed. Engl., vol. 34, p. 1143–1170 (1995), European Patent Application 416,815 and U.S. Pat. No. 5,198,401 for information about metallocene-type catalysts, and J. Boor Jr., Ziegler-Natta Catalysts and Polymerizations, Academic Press, New York, 1979 for information about Ziegler-Natta-type catalysts, all of which are hereby included by reference. Suitable late metal transition catalysts will be found in World Patent Applications 96/23010 and 97/02298, both of which are hereby included by reference. Many of the useful polymerization conditions for these types of catalyst and the first active polymerization catalysts coincide, so conditions for the polymerizations with first and second active polymerization catalysts are easily accessible. Oftentimes the "cocatalyst" or "activator" is needed for metallocene of Ziegler-Natta-type polymerizations, much as W is sometimes needed for polymerizations using the first active polymerization catalysts. In many instances the same compound, such as an alkylaluminum compound, may be used for these purposes for both types of polymerization catalysts.

Suitable catalysts for the second polymerization catalyst also include metallocene-type catalysts, as described in U.S. Pat. No. 5,324,800 and European Patent Application 129,368; particularly advantageous are bridged bis-indenyl metallocenes, for instance as described in U.S. Pat. No. 5,145,819 and European Patent Application 485,823. Another class of suitable catalysts comprises the well-known constrained geometry catalysts, as described in European Patent Applications 416,815, 420,436, 671,404, and 643,066 and World Patent Application 91/04257. Also the class of transition metal complexes described in WO 96/13529 can be used. Also useful are transition metal complexes of bis(carboximidamidatonates), as described in U.S. patent application Ser. No. 08/096,668, filed Sep. 1, 1998.

All the catalysts herein may be "heterogenized" (to form a polymerization catalyst component, for instance) by coating or otherwise attaching them to solid supports, such as silica or alumina. Where an active catalyst species is formed by reaction with a compound such as an alkylaluminum compound, a support on which the alkylaluminum compound is first coated or otherwise attached is contacted with the transition metal compounds (or their precursors) to form a catalyst system in which the active polymerization catalysts are "attached" to the solid support. These supported catalysts may be used in polymerizations in organic liquids. They may also be used in so-called gas phase polymerizations in which the olefin(s) being polymerized are added to the polymerization as gases and no liquid supporting phase is present. The transition metal compounds-may also be coated onto a support such as a polyolefin (polyethylene, polypropylene, etc.) support, optionally along with other needed catalyst components such as one or more alkylaluminum compounds.

The molar ratio of the first active polymerization catalyst to the second active polymerization catalyst used will depend on the ratio of polymer from each catalyst desired, and the relative rate of polymerization of each catalyst under the process conditions. For instance, if one wanted to prepare a "toughened" thermoplastic polyethylene that contained 80% crystalline polyethylene and 20% rubbery polyethylene, and the rates of polymerization of the two catalysts were equal, then one would use a 4:1 molar ratio of the catalyst that gave crystalline polyethylene to the catalyst that gave rubbery polyethylene. More than two active polymerization catalysts may also be used if the desired product is to contain more than two different types of polymer.

The polymers made by the first active polymerization catalyst and the second active polymerization catalyst may be made in sequence, i.e., a polymerization with one (either first or second) of the catalysts followed by a polymerization with the other catalyst, as by using two polymerization vessels in series. However it is preferred to carry out the polymerization using the first and second active polymerization catalysts in the same vessel(s), i.e., simultaneously. This is possible because in most instances the first and second active polymerization catalysts are compatible with each other, and they produce their distinctive polymers in the other catalyst's presence.

The polymers produced by this process may vary in molecular weight and/or molecular weight distribution and/or melting point and/or level of crystallinity, and/or glass transition temperature or other factors. For copolymers the polymers may differ in ratios of comonomers if the different polymerization catalysts polymerize the monomers present at different relative rates. The polymers produced are useful as molding and extrusion resins and in films as for packaging. They may have advantages such as improved melt processing, toughness and improved low temperature properties.

In the Examples, all pressures are gauge pressures.

In the Examples the transition metal catalysts were either bought, or if a vendor is not listed, were made. Synthesis of nickel containing catalysts will be found in World Patent Application 96/23010, while synthesis of cobalt and iron containing catalysts will be found in U.S. patent application Ser. No. 08/991,372, filed Dec. 16, 1997 U.S. Pat. No. 5,955,555 and Ser. No. 09/006,031, filed Jan. 12, 1998 U.S. Pat. No. 6,150,482.

In the Examples PMAO-IP is a form of methylaluminoxane which stays in solution in toluene, and is commercially available. W440 is a Ziegler-Natta type catalyst of unknown structure available from Akzo Chemicals, Inc., 1 Livingston Ave., Dobbs Ferry, N.Y. 10522, U.S.A.

EXAMPLES 1–9 AND COMPARATIVE EXAMPLES A–E

Ethylene Polymerization General Procedure

The catalyst was weighed into a reaction vessel and was dissolved in about 20 mL of distilled toluene. The reaction was sealed and transferred from the drybox to the hood. The reaction was purged with nitrogen, then ethylene. The PMAO-IP (methylaluminoxane solution) was then quickly added to the vessel and the reaction was put under 35 kPa ethylene. The reaction ran at room temperature in a water bath to help dissipate heat from any exotherm. The ethylene was then turned off and the reaction was quenched with about 15 mL of methanol/HCl solution (90/10 volume %). If polymer was present, the reaction was filtered and the polymer was rinsed with methanol, then acetone and dried overnight in the hood. The resulting polymer was collected and weighed.

Below for each polymerization the catalysts used are listed:

EXAMPLE 1 catalyst 1: 4 mg (0.006 mmol)

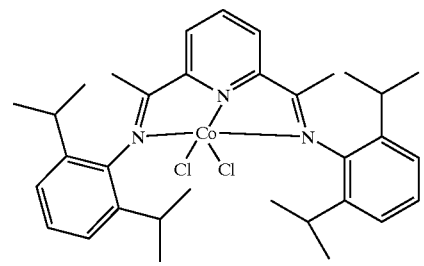

catalyst 2: Zirconocene dichloride, from Strem Chemicals, catalog #93-4002, 2 mg (0.006 mmol)

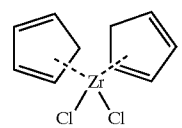

co-catalyst: PMAO-IP; 2.0 mmole Al; 1.0 mL of 2.0M in toluene duration: 4 h polymer: 5.322 g yield

EXAMPLE 2 catalyst 1: 4 mg (0.006 mmol)

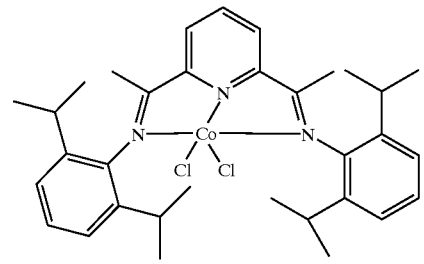

catalyst 2: 4 mg (0.006 mmol)

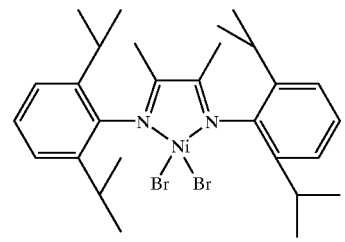

cocatalyst: PMAO-IP; 2.0 mmol Al; 1.0 mL of 2.0M in toluene duration: 4 h polymer: 2.282 g yield

EXAMPLE 3 catalyst 1: 3.5 mg (0.006 mmol)

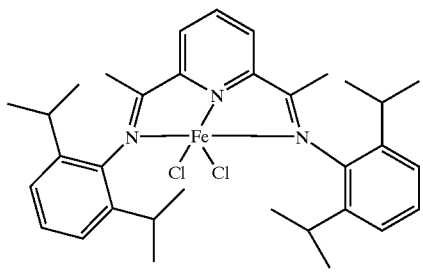

catalyst 2: Zirconocene dichloride, from Strem Chemicals, catalog #93-4002, 2 mg (0.006 mmol)

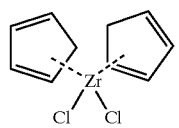

cocatalyst: PMAO-IP; 2.0 mmol Al; 1.0 mL of 2.0M in toluene duration: 4 h polymer: 3.651 g yield

EXAMPLE 4 catalyst 1: 3.5 mg (0.006 mmole)

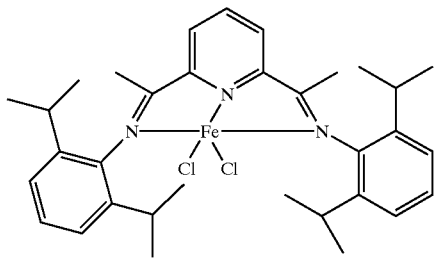

catalyst 2: 4 mg (0.006 mmol)

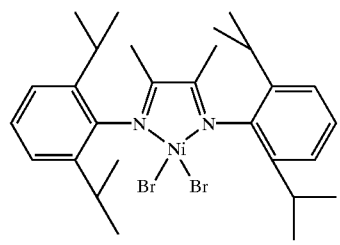

cocatalyst: PMAO-IP; 2.0 mmol Al; 1.0 mL of 2.0M in toluene duration: 4 h polymer: 2.890 g yield

EXAMPLE 5 catalyst 1: 3.5 mg (0.006 mmol)

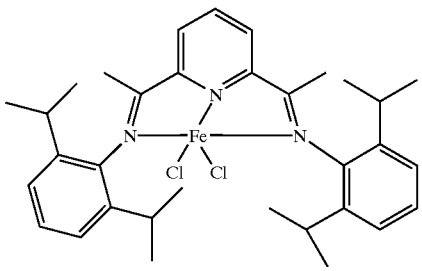

catalyst 2: 4 mg (0.006 mmol)

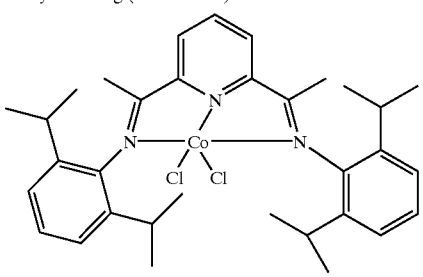

cocatalyst: PMAO-IP; 2.0 mmole Al; 1.0 mL of 2.0M in toluene duration: 4 h polymer: 3.926 g yield

EXAMPLE 6 catalyst 1: 4 mg (0.006 mmol)

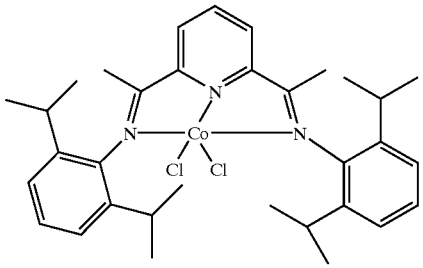

catalyst 2: W440, from Akzo Nobel, 2.3 wt % Ti, 12 mg (0.006 mmole of Ti, based on wt %)

cocatalyst: PMAO-IP; 2.0 mmole Al; 1.0 mL of 2.0M in toluene duration: 4 h polymer: 2.643 g yield

EXAMPLE 7 catalyst 1: 3.5 mg (0.006 mmol)

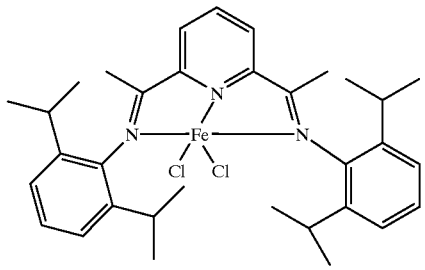

catalyst 2: W440, from Akzo Nobel, 2.3 wt % Ti, 12 mg (0.006 mmole of Ti, based on wt %)

cocatalyst: PMAO-IP; 2.0 mmol Al; 1.0 mL of 2.0M in toluene duration: 4 h polymer: 2.943 g yield

EXAMPLE 8 catalyst 1: 4 mg (0.006 mmol)

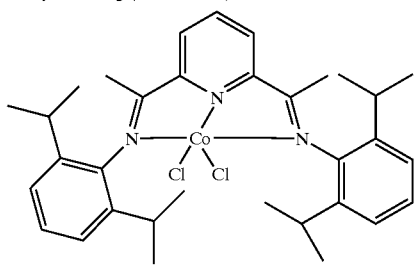

catalyst 2: 4 mg (0.006 mmol)

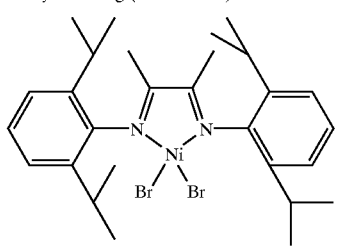

catalyst 3: Zirconocene dichloride, from Strem Chemicals, catalog #93-4002, 2 mg (0.006 mmol)

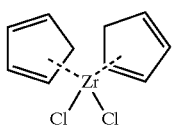

cocatalyst: PMAO-IP; 3.0 mmol Al; 1.5 mL of 2.0M in toluene duration: 4 h polymer: 6.178 g yield

EXAMPLE 9 catalyst 1: 3.5 mg (0.006 mmol)

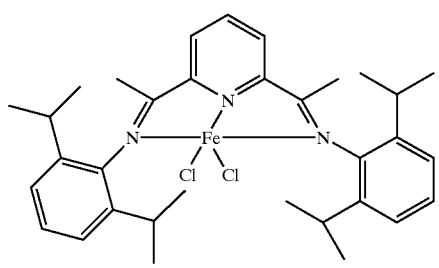

catalyst 2: 4 mg (0.006 mmol)

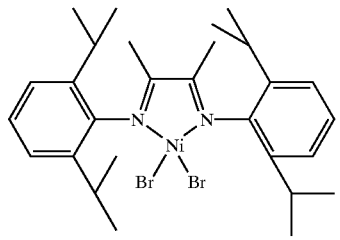

catalyst 3: Zirconocene dichloride, from Strem Chemicals, catalog #93-4002, 2 mg (0.006 mmol)

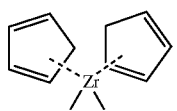

cocatalyst: PMAO-IP; 3.0 mmol Al; 1.5 mL of 2.0M in toluene duration: 4 h polymer: 4.408 g yield

Comparative Example A catalyst: Zirconocene dichloride, from Strem Chemicals, catalog #93-4002, 2 mg (0.006 mmol)

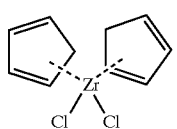

cocatalyst: PMAO-IP; 1.0 mmol Al; 0.5 mL of 2.0M in toluene duration: 4 h polymer: 2.936 g yield

Comparative Example B catalyst: 4 mg (0.006 mmol)

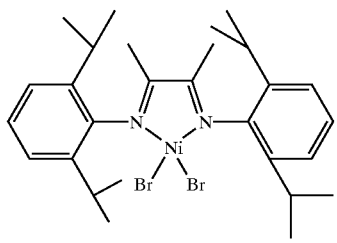

cocatalyst: PMAO-IP; 1.0 mmol Al; 0.5 mL of 2.0M in toluene
duration: 4 h
polymer: 1.053 g yield

Comparative Example C catalyst: 4 mg (0.006 mmol)

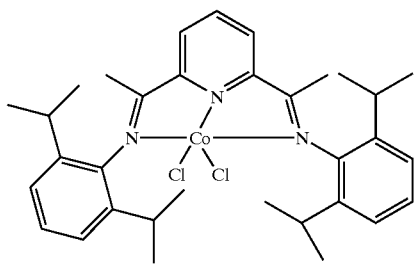

cocatalyst: PMAO-IP; 1.0 mmol Al; 0.5 mL of 2.0M in toluene
duration: 4 h
polymer: 2.614 g yield

Comparative Example D catalyst: 3.5 mg (0.006 mmol)

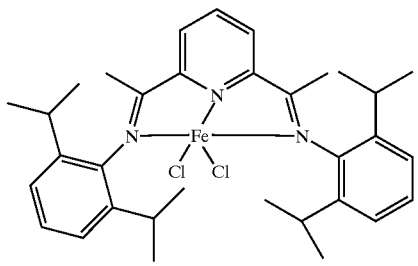

cocatalyst: PMAO-IP; 1.0 mmol Al; 0.5 mL of 2.0M in toluene
duration: 4 h
polymer: 2.231 g yield

Comparative Example E catalyst: W440, from Akzo Nobel, 2.3 wt % Ti, 12 mg (0.006 mmole of Ti, based on wt %)
cocatalyst: PMAO-IP; 1.0 mmol Al; 0.5 mL of 2.0M in toluene
duration: 4 h
polymer: 0.326 g yield

EXAMPLES 10–12

Propylene Polymerization General Procedure

The catalyst was weighed into a reaction vessel and was dissolved in about 20 mL of distilled toluene. The reaction was sealed and transferred from the drybox to the hood. The reaction was purged with nitrogen, then propylene. The MAO was then quickly added to the vessel and the reaction was put under 35 kPa propylene. Reaction ran at 0° C. in an ice bath. The propylene was then turned off and the reaction was quenched with about 15 mL of methanol/HCl solution (90/10 volume %). If polymer was present, the reaction was filtered and the polymer was rinsed with methanol, then acetone and dried overnight in the hood. The resulting polymer was collected and weighed.

EXAMPLE 10 catalyst 1: 3 mg (0.006 mmol)

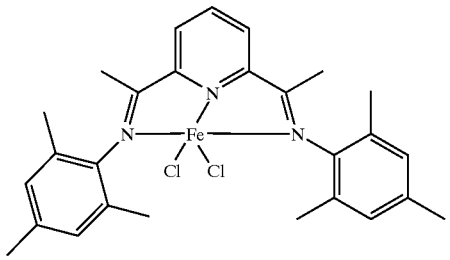

catalyst 2: Zirconocene dichloride, from Strem Chemicals, catalog #93-4002, 2 mg (0.006 mmol)

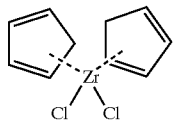

cocatalyst: PMAO-IP; 2.0 mmol Al; 1.0 mL of 2.0M in toluene duration: 5 h polymer: 0.471 g yield

EXAMPLE 11 catalyst 1: 3 mg (0.006 mmol)

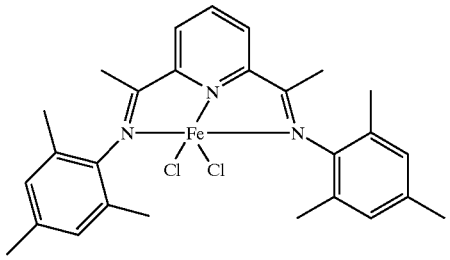

-continued catalyst 2: 4 mg (0.006 mmol)

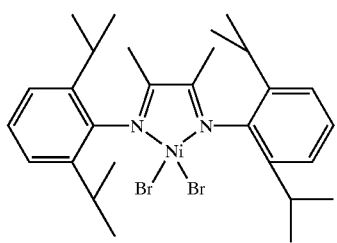

cocatalyst: PMAO-IP; 2.0 mmole Al; 1.0 mL of 2.0M in toluene duration: 5 h polymer: 1.191 g yield

EXAMPLE 12 catalyst 1: 3 mg (0.006 mmol)

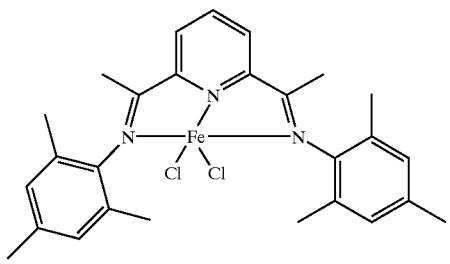

catalyst 2: W440, from Akzo Nobel, 2.3 wt % Ti, 12 mg (0.006 mmole of Ti, based on wt %)

cocatalyst: PMAO-IP; 2.0 mmol Al; 1.0 mL of 2.0M in toluene duration: 5 h polymer: 0.238 g yield

EXAMPLE 13–17 AND COMPARATIVE EXAMPLES F–N

In these Examples, compounds A–V and 2 were used as the transition metal compounds.

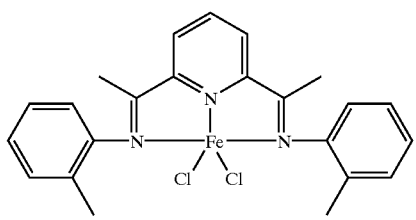

A

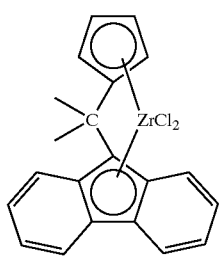

B

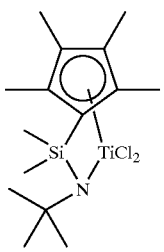

C

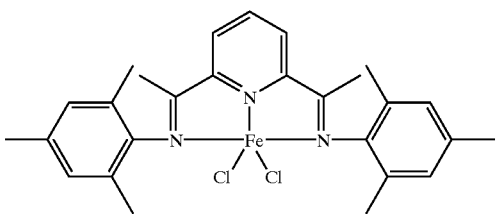

D

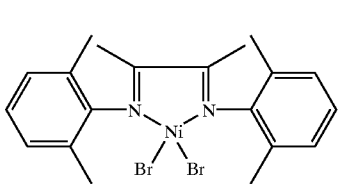

E

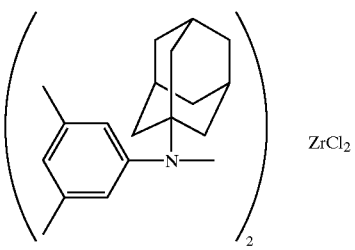

F

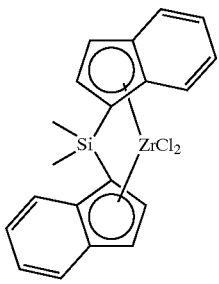

G

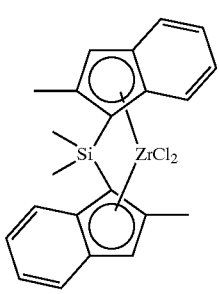

H

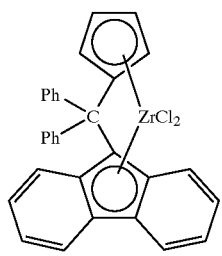
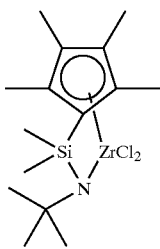
I
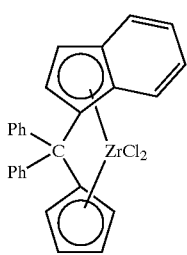
J
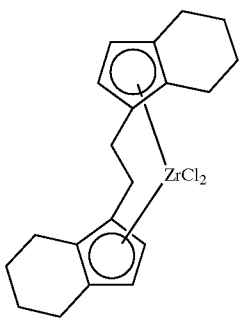
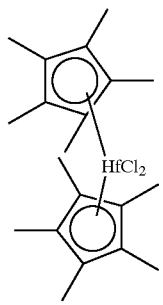
K
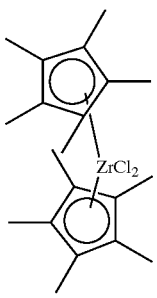
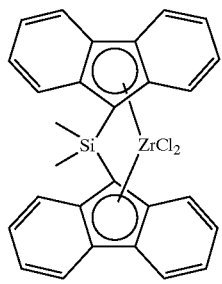
L
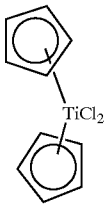
M
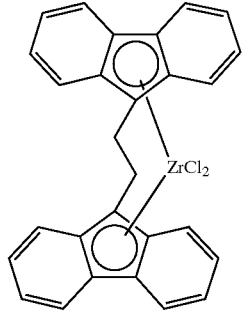
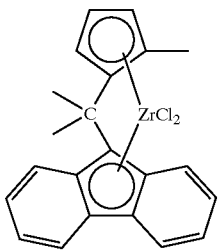

-continued

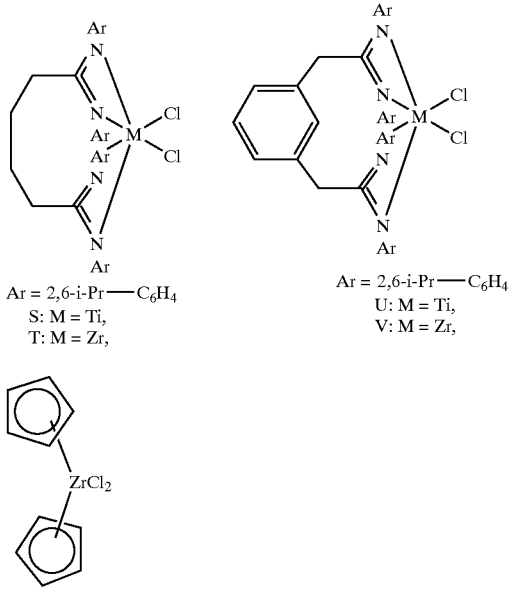

For preparation of: compound A see B. L. Small, et al., J. Am. Chem. Soc., vol. 120, p. 7143–7144(1998); compound B see Ewen, et al., J. Am. Chem. Soc., vol. 110, p. 6255–6256(1988); compound C see European Patent Application 416,815; compound D World patent Application 98/27124; compound E World patent Application 96/23010; compounds G, H, I and R were purchased from Boulder Scientific company; compounds K, P and 2 were bought from Strem Chemicals Inc.; compound Q was obtained from Aldrich Chemical Co.; compounds S, T, U and V were made by procedures described in U.S. patent application Ser. No. 08/096,668, filed Sep. 1, 1998 U.S. Pat. No. 5,337,529; compound F was made by reacting $ZrCl_4$ and the amide lithium salt (see J. Chem. Soc., Dalton Trans. 1994, 657) in ether overnight, and removing the ether and pentane extraction gave F 69% yield; compound J was prepared by modifying the procedure of Journal of Organometallic Chemistry 1993, 459, 117–123; compounds L and M were prepared by following the preparation in Macromolecules, 1995, 28, 5399–5404, and Journal of Organometallic Chemistry 1994, 472, 113–118; compound N was made by the procedure described in U.S. Pat. No. 5,096,867; and compound O was prepared by following a literature procedure (Ferdinand R. W. P. Wild, et al., Journal of Organometallic Chemistry 1985, 288, 63–67).

EXAMPLES 13–17 AND COMPARATIVE EXAMPLES F–G

A 600 mL Parr® reactor was heated up under vacuum and then allowed to cool under nitrogen. In a drybox, to a Hoke® cylinder was added 5 mL toluene and a certain amount of PMAO-IP (13.5 wt % toluene solution) as shown in Table 1. To a 20 mL vial was added the ethylene (co)polymerization catalyst and 2 mL toluene. The solution was then pipette transferred to a 300 mL RB flask, followed by addition of 150 mL 2,2,4-trimethyl pentane. If catalyst A was used, its toluene suspension was syringe transferred to the flask. The flask was capped with a rubber septa. Both the Hoke® cylinder and the flask were brought out of the drybox. Under nitrogen protection, the transition metal compound solution was cannulated to the reactor. The reactor was pressurized with nitrogen and then the nitrogen was released. The reactor was heated to 70° C., then, pressurized 2x to 690 kPa ethylene, venting each time and finally pressurized to 970 kPa with stirring. The MAO solution was added from the Hoke® cylinder at slightly higher pressure. The ethylene pressure of the reactor was then adjusted to the desired pressure (Table 1). The reaction mixture was allowed to stir for certain period of time (Table 1). The heating source was removed. Ethylene was vented to about 210 kPa. The reactor was back filled with 1.4 MPa nitrogen and was then vented to 210 kPa. This was repeated once. The reaction mixture was then cooled to RT (room temperature). The reaction mixture was then slowly poured into 400 mL methanol, followed by addition of 6 mL conc. HCl. Upon stirring at RT for 25 min, polymer was filtered, washed with methanol six times and dried in vacuo.

EXAMPLES 18–76 (EXCEPT EXAMPLES 22 AND 23) AND COMPARATIVE EXAMPLES H–N

General procedure for making silica supported catalysts: In a drybox, one of transition metal compounds (but not A), and compound A (0.1 wt % in biphenyl) and silica supported MAO (18 wt % in Al, Albermarle) were mixed with 15 mL of toluene in a 20 mL vial. The vial was shaken for 45 minutes at RT. The solid was filtered, washed with 3×5 mL toluene and dried in vacuo for 1 hour. It was then stored in a freezer in the drybox and was used the same day.

General procedure for gas phase ethylene polymerization by the supported catalysts using a multitube block reactor: In a drybox, supported catalysts (5.0 mg or 2.0 mg each, except Example 20 where 15.0 mg was used) were weighed in GC vials. They were placed in a Harper Block Reactor. The reactor was brought out of the drybox and was charged with 1.21 MPa of ethylene. It was then placed in a 90° C. oil bath for 1 h under 1.12 MPa of ethylene. The reactor temperature reached 85° C. after 23 minutes and 87° C. after 35 min. The temperature stayed at 87° C. for the rest of the reaction. (Time, temperature and pressure for Examples in Tables 7–9, as noted.) Ethylene was vented. Polymers were weighed and then submitted for $^1$H NMR analysis (TCE-$d_2$, 120° C.) without purification. Details of these polymerizations are given in Table 2–9.

In Table 10, the branching distribution [in branches per 1,000 methylene ($CH_2$) groups] of the product polymers of selected examples are given. They were determined by $^{13}$C NMR (TCB, 120° C.). Methods for measuring the branching distribution are found in World patent Application 96/23010.

In all the Tables, where provided, branching levels in the polymers, Me/1000$CH_2$ groups, methyl groups per 1000 methylene groups in the polymer, are measured by the method described in World Patent Application 96/23010. In the Tables PE is polyethylene, TON is moles of ethylene polymerized/mole of polymerization catalysts (total of transition metal compounds present)/h, Mn is number average molecular weight, PDI is Mw/Mn where Mw is weight average molecular weight, and P is ethylene pressure. The PMAO-IP used was 13.5 wt. % in toluene. The amount of residual α-olefin in the polymer was estimated by $^1$H NMR, by measurement of the vinylic proton signals of the α-olefin.

TABLE 1

| Ex. No. | Catalyst, amount (×10⁻⁶ mole) | Catalyst A (×10⁻⁶ mole) | $P_{C_2H_4}$ MPa | T(° C.) | Time (min.) | MMAO (mL) | PE yield (g) | #Me Per 1000CH₂ | m.p. (° C.) | Mn/PDI | Density(IR) (g/cm³) |
|---|---|---|---|---|---|---|---|---|---|---|---|
| F  | B, 8.1 | 0    | 1.21 | 70–100  | 35 | 4.2 | 15.0 | 1  | 134     | 43,700/2.2              | 0.952 |
| 13 | B, 8.1 | 0.26 | 1.31 | 81–96   | 25 | 4.2 | 24.0 | 17 | 116, 103| 32,400/2.2              | 0.914 |
| G  | C, 2.2 | 0    | 1.1  | 90      | 30 | 1.2 | 11.0 | 4  | 132     | 11,700/19.7             | 0.940 |
| 14 | C, 9.5 | 0.06 | 1.31 | 109–126 | 30 | 4.8 | 31.2 | 8  | 133     | 125,000/2.7             | 0.937 |
| 15 | C, 9.5 | 0.13 | 1.34 | 80–120  | 36 | 4.8 | 30.0 | 11 | 119     | 68,400/2.5              | 0.922 |
| 16 | C, 4.6 | 0.26 | 1.3  | 71–96   | 25 | 2.4 | 10.3 | 45 | 121, 56 | 94,000/2.3 261/2.8*     | 0.895 |
| 17 | C, 3.0 | 2.3  | 1.41 | 100–116 | 43 | 1.5 | 16.6 | 52 | 117, 98 84 | 65,000/2.1 214/3.4*  | 0.922 |

*Bimodal distribution due to α-olefins

TABLE 2

| Ex. No. | Catalyst and amount (×10⁻⁶ mole) | Catalyst A (×10⁻⁶ mole) | Al:M:Fe ratio M = Zr, Ti or Fe | PE yield (g) | #Me/1000CH₂ | Tm (° C.) | Mn/PDI | TON |
|---|---|---|---|---|---|---|---|---|
| H  | B, 0.033 | 0      | 1000:1:0    | 0.195 | 5  | 127 | 24,039/5.2   | 210,000 |
| I  | C, 0.033 | 0      | 1000:1:0    | 0.075 | 4  | 126 | 125,451/2.1  | 82,000  |
| 18 | B, 0.033 | 0.001  | 1000:1:0.03 | 0.485 | 15 | 120 | 48,213/4.1   | 500,000 |
| 19 | B, 0.033 | 0.0033 | 1000:1:0.1  | 0.159 | 62 | 125 | 1,916/24.0   | 150,000 |
| 20 | C, 0.099 | 0.0030 | 1000:1:0.03 | 0.200 | 35 | 113 | 63,534/2.7   | 70,000  |
| 21 | D, 0.033 | 0.0017 | 1000:1:0.05 | 0.228 | 4  | 133 | 2,150/26.2   | 240,000 |

TABLE 3

| Ex. No. | Catalyst and amount (×10⁻⁶ mole) | Catalyst A (×10⁻⁶ mole) | Al:M:Fe ratio M = Zr, Ti or Fe | PE yield (g) | #Me/1000CH₂ | TON |
|---|---|---|---|---|---|---|
| J | H, 0.033 | 0 | 1000:1:0 | 0.421 | 2 | 460,000 |
| K | I, 0.033 | 0 | 1000:1:0 | 0.135 | 4 | 150,000 |
| L | G, 0.033 | 0 | 1000:1:0 | 0.420 | 2 | 460,000 |
| M | K, 0.033 | 0 | 1000:1:0 | 0.091 | 3 | 99,000  |
| N | R, 0.033 | 0 | 1000:1:0 | 0.203 | 2 | 220,000 |

TABLE 4

| Ex. No. | Catalyst and amount (×10⁻⁶ mole) | Catalyst A (×10⁻⁶ mole) | Al:M:Fe ratio M = Zr, Ti or Fe | PE yield (g) | #Me/1000CH₂ | Tm (° C.) | Mn/PDI | TON | α-olefins left in polymer |
|---|---|---|---|---|---|---|---|---|---|
| 24 | F, 0.033 | 0.0017 | 1000:1:0.05 | 0.073 | 66 | 120      | 213/18.5    | 76,000  | significant |
| 25 | G, 0.033 | 0.0017 | 1000:1:0.05 | 0.503 | 13 | 122, 115 | 41,525/4.7  | 520,000 | almost none |
| 26 | H, 0.033 | 0.0017 | 1000:1:0.05 | 0.752 | 9  | 120, 115 | 54,825/4.7  | 780,000 | almost none |
| 27 | I, 0.033 | 0.0017 | 1000:1:0.05 | 0.562 | 31 | 119      | 72,982/3.2  | 580,000 | almost none |
| 28 | J, 0.033 | 0.0017 | 1000:1:0.05 | 0.032 | 54 | —        | 895/5.6     | 33,000  | small amount |
| 29 | K, 0.033 | 0.0017 | 1000:1:0.05 | 0.240 | 16 | 123      | 1,124/16.5  | 250,000 | small amount |
| 30 | L, 0.033 | 0.0017 | 1000:1:0.05 | 0.112 | 75 | 116, 102 | —           | 116,000 | significant |
| 31 | M, 0.033 | 0.0017 | 1000:1:0.05 | 0.092 | 61 | 119      | —           | 96,000  | significant |
| 32 | N, 0.033 | 0.0017 | 1000:1:0.05 | 0.068 | 75 | 124      | 485/18.3    | 71,000  | small amount |
| 33 | O, 0.033 | 0.0017 | 1000:1:0.05 | 0.024 | 15 | —        | —           | 25,000  | almost none |
| 34 | P, 0.033 | 0.0017 | 1000:1:0.05 | 0.019 | 12 | —        | —           | 20,000  | small amount |
| 35 | Q, 0.033 | 0.0017 | 1000:1:0.05 | 0.082 | 40 | —        | —           | 85,000  | significant |
| 36 | 2, 0.033 | 0.0017 | 1000:1:0.05 | 0.157 | 7  | —        | —           | 160,000 | —           |
| 37 | R, 0.033 | 0.0017 | 1000:1:0.05 | 0.416 | 10 | 122      | 37,993/7.3  | 450,000 | almost none |
| 38 | S, 0.033 | 0.0017 | 1000:1:0.05 | 0.056 | 59 | —        | —           | 58,000  | significant |
| 39 | T, 0.033 | 0.0017 | 1000:1:0.05 | 0.023 | 73 | —        | —           | 24,000  | significant |
| 40 | U, 0.033 | 0.0017 | 1000:1:0.05 | 0.102 | 69 | —        | —           | 110,000 | significant |
| 41 | V, 0.033 | 0.0017 | 1000:1:0.05 | 0.059 | 78 | —        | —           | 61,000  | significant |

TABLE 5*

| Ex. No. | Catalyst and amount ($\times 10^{-6}$ mole) | Catalyst A ($\times 10^{-6}$ mole) | Al:M:Fe ratio M = Zr, Ti or Fe | PE Yield (g) | #Me/ 1000CH$_2$ | Mn/PDI | TON | α-olefins left in polymer |
|---|---|---|---|---|---|---|---|---|
| 42 | D, 0.033 | 0.0033 | 1000:1:0.10 | 0.481 | 8 | 3,346/48.6 | 360,000 | significant |
| 43 | D, 0.033 | 0.0082 | 1000:1:0.25 | 0.534 | 14 | 402/156.0 | 350,000 | significant |
| 44 | D, 0.033 | 0.016 | 1000:1:0.50 | 0.566 | 20 | 800/103.0 | 310,000 | significant |

*Reaction time here is 80 minutes

TABLE 6

| Ex. No. | Catalyst and amount ($\times 10^{-6}$ mole) | Catalyst A ($\times 10^{-6}$ mole) | Al:M:Fe ratio M = Zr, Ti or Fe | PE yield (g) | #Me/ 1000CH$_2$ | Tm (°C.) | Mn/PDI | TON | Density (g/cm$^3$) |
|---|---|---|---|---|---|---|---|---|---|
| 45 | H, 0.033 | 0.0017 | 1000:1:0.05 | 0.772 | 6 | 124 | 43,791/6.0 | 800,000 | 0.930 |
| 46 | H, 0.013 | 0.0007 | 1000:1:0.05 | 0.367 | 8 | 124 | 82,151/3.7 | 950,000 | — |
| 47 | I, 0.033 | 0.0017 | 1000:1:0.05 | 0.566 | 38 | 114 | 70,462/4.0 | 590,000 | 0.909 |
| 48 | I, 0.013 | 0.0007 | 1000:1:0.05 | 0.226 | 32 | — | — | 590,000 | — |
| 49 | B, 0.033 | 0.0010 | 1000:1:0.03 | 0.442 | 8 | 127 | 52,673/4.9 | 460,000 | 0.928 |
| 50 | B, 0.033 | 0.0010 | 1000:1:0.03 | 0.563 | 17 | 120 | 52,350/4.9 | 600,000 | — |
| 51 | B, 0.013 | 0.0004 | 1000:1:0.03 | 0.134 | 16 | — | — | 350,000 | — |
| 52 | H, 0.033 | 0.0010 | 1000:1:0.03 | 0.699 | — | — | — | 740,000 | — |
| 53 | N, 0.013 | 0.0004 | 1000:1:0.03 | 0.362 | 6 | 124 | 55,102/5.0 | 960,000 | — |
| 54 | I, 0.033 | 0.0010 | 1000:1:0.03 | 0.376 | 15 | 118 | 98,599/4.0 | 400,000 | — |
| 55 | G, 0.033 | 0.0010 | 1000:1:0.03 | 0.665 | 5 | 124 | 38,693/6.0 | 700,000 | — |

TABLE 7*

| Ex. No. | Catalyst and amount ($\times 10^{-6}$ mole) | Catalyst A ($\times 10^{-6}$ mole) | Al:M:Fe ratio M = Zr, Ti or Fe | PE Yield (g) | #Me/ 1000CH$_2$ | Tm (°C.) | Mn/PDI | TON |
|---|---|---|---|---|---|---|---|---|
| 56 | B, 0.033 | 0.0017 | 1000:1:0.05 | 0.740 | 22 | 118,101 | 54,734/4.0 | 380,000 |
| 57 | B, 0.013 | 0.0007 | 1000:1:0.05 | 0.206 | 24 | — | — | 270,000 |
| 58 | H, 0.033 | 0.0017 | 1000:1:0.05 | 1.158 | 7 | 121 | 92,063/4.9 | 600,000 |
| 59 | H, 0.013 | 0.0007 | 1000:1:0.05 | 0.651 | 12 | — | — | 850,000 |
| 60 | I, 0.033 | 0.0017 | 1000:1:0.05 | 0.439 | 24 | 102 | 102,798/3.8 | 230,000 |
| 61 | I, 0.013 | 0.0007 | 1000:1:0.05 | 0.390 | 25 | — | — | 510,000 |
| 62 | G, 0.033 | 0.0017 | 1000:1:0.05 | 0.871 | 9 | 121 | 45,311/4.7 | 450,000 |

*Two h at 70° C. and 2.4 MPa ethylene pressure.

TABLE 8*

| Ex. No. | Catalyst and amount ($\times 10^{-6}$ mole) | Catalyst A ($\times 10^{-6}$ mole) | Al:M:Fe ratio M = Zr, Ti or Fe | PE yield (g) | TON |
|---|---|---|---|---|---|
| 63 | B, 0.013 | 0.0007 | 1000:1:0.05 | 0.143 | 370,000 |
| 64 | B, 0.013 | 0.0007 | 1000:1:0.05 | 0.115 | 300,000 |
| 65 | H, 0.013 | 0.0007 | 1000:1:0.05 | 0.305 | 790,000 |
| 66 | H, 0.013 | 0.0007 | 1000:1:0.05 | 0.215 | 560,000 |
| 67 | I, 0.013 | 0.0007 | 1000:1:0.05 | 0.093 | 240,000 |
| 68 | I, 0.013 | 0.0007 | 1000:1:0.05 | 0.108 | 280,000 |
| 69 | G, 0.013 | 0.0007 | 1000:1:0.05 | 0.349 | 900,000 |

One h at 90° C. at 2.4 MPa ethylene pressure.

TABLE 9*

| Ex. No. | Catalyst and amount ($\times 10^{-6}$ mole) | Catalyst A ($\times 10^{-6}$ mole) | Al:M:Fe ratio M = Zr, Ti or Fe | PE yield (g) | #Me/ 1000CH$_2$ | Mn/PDI | TON |
|---|---|---|---|---|---|---|---|
| 70 | B, 0.033 | 0.0017 | 1000:1:0.05 | 0.534 | 37 | 42,448/3.4 | 280,000 |
| 71 | B, 0.033 | 0.0017 | 1000:1:0.05 | 0.489 | 45 | — | 250,000 |
| 72 | H, 0.033 | 0.0017 | 1000:1:0.05 | 0.969 | 17 | 77,142/4.8 | 500,000 |

TABLE 9*-continued

| Ex. No. | Catalyst and amount (×10⁻⁶ mole) | Catalyst A (×10⁻⁶ mole) | Al:M:Fe ratio M = Zr, Ti or Fe | PE yield (g) | #Me/ 1000CH$_2$ | Mn/PDI | TON |
|---|---|---|---|---|---|---|---|
| 73 | H, 0.033 | 0.0017 | 1000:1:0.05 | 1.027 | 11 | — | 530,000 |
| 74 | I, 0.033 | 0.0017 | 1000:1:0.05 | 0.442 | 34 | 96,383/4.2 | 230,000 |
| 75 | I, 0.033 | 0.0017 | 1000:1:0.05 | 0.466 | 32 | — | 240,000 |
| 76 | G, 0.033 | 0.0017 | 1000:1:0.05 | 0.710 | 8 | 39,693/4.9 | 370,000 |

*Two h at 60° C., 2.4 MPa ethylene pressure

TABLE 10

| Ex. No. | Total Me | Me | Et | Pr | Bu | Am | Hex and higher |
|---|---|---|---|---|---|---|---|
| 15 | 10.5 | 0 | 4.6 | 0 | 2.4 | 0 | 4.3 |
| 13 | 16 | 0 | 6.5 | 0 | 3.2 | 0 | 6.5 |
| 26 | 6.9 | 0 | 2.9 | 0 | 0.4 | 0 | 2.5 |
| 47 | 23 | 0 | 8.6 | 0 | 4.7 | 0 | 10.7 |
| 49 | 8.1 | 0 | 3.6 | 0 | 1.3 | 0 | 3.1 |

EXAMPLE 22

In a drybox, 1.7 mg Compound E and 1.0 mg Compound A were mixed with 40 mL toluene in a Schlenk flask. This was brought out of the drybox and was purged with ethylene for 15 min at 0° C. MAO toluene solution (0.64 mL 13.5 wt %) was injected. The mixture was allowed to stir under 0 kPa ethylene at 0° C. for 12 min. Methanol (100 mL) was injected, followed by 1 mL conc. HCl. Upon stirring for 25 min at RT, the white solid was filtered, washed with 6×20 mL methanol and dried in vacuo. White solid (2.9 g) was obtained. $^1$HNMR in TCE-d$_2$ at 120° C.: 44Me/1000CH$_2$. The polymer contained a significant amount of α-olefins.

EXAMPLE 23

In a drybox, 30.5 mg of Compound A was mixed with 30.5 g biphenyl in a 100 mL Pyrex® glass bottle. This was stirred in a 100° C. bath for 25 minutes, during which time Compound A dissolved in biphenyl to form a deep green solution. The solution was allowed to cool down to become solid. A 0.1 wt % Compound A/biphenyl homogeneous mixture was obtained.

EXAMPLE 24

A 600 mL Parr® reactor was heated up under vacuum and then allowed to cool under nitrogen. In a drybox, to a 300 mL RB flask was added 150 mL 2,2,4-trimethylpentane. The flask was capped with a rubber septum. The flask was brought out of the drybox. Under nitrogen protection, the 2,2,4-trimethylpentane solvent was cannulated into the reactor. The reactor was pressured up with nitrogen and then nitrogen was released. This was repeated one more time. The reactor was heated to 70° C. Then in a drybox, 160 mg supported catalyst(made by following the general procedure of preparing silica supported catalysts, it contained 0.0011 mmole of compound B, 0.000057 mmole compound A and 1.1 mmole of MAO) was mixed with 4 mL cyclohexane and was transferred to a 5 mL gas tight syringe with long needle. This was brought out of the drybox and was injected into the reactor under nitrogen protection (positive nitrogen pressure). The reactor was pressured up with 1.2 MPa of nitrogen, then released to 14 kPa. This was repeated one more time. Under stirring, the reactor was pressured up with ethylene to 1.2 MPa. The reaction mixture was allowed to stir at between 70° C. to 97° C. for 60 min. Heating source was removed. Ethylene was vented to about 210 kPa. The reactor was back filled with 1.4 MPa nitrogen and was released to 140 kPa. This was repeated twice. The solution was poured into 300 mL methanol. The polymer was filtered, washed with 6×50 mL methanol and dried in vacuo. White polymer (19.7 g) was obtained. $^1$HNMR in TCE-d$_2$ at 120° C.: 34Me/1000CH$_2$. Mw=98,991; Mn=35,416(PDI=2.8). Density: 0.902 g/cm$^3$. Melt Index: 1.03(190° C). $^{13}$CNMR(120° C., TCE-d$_2$): Total Me was 29.4(Me=0; Et=10.8; Pr=0.0; Bu=6.0; Hex and higher=11.7).

EXAMPLES 25–30

In these Examples, all pressures are gauge pressures. The following transition metal compounds are used in the catalyst systems. A is an ethylene oligomerization catalyst, while B is an ethylene and α-olefin copolymerization catalyst.

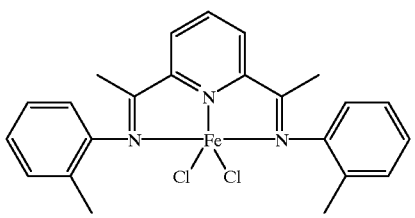

A

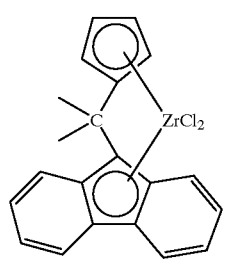

B

A is made by methods described in World Patent Application 99/02472, while B may be made as described in Ewen, et al., J. Am. Chem. Soc., vol. 110, p. 6255–6256 (1988).

In these Examples, the following abbreviations are used:
DSC—differential scanning calorimetry
GPC—gel permeation chromatography
MAO—methylaluminoxane
MAO-IP—an MAO with improved toluene solubility
MI—melt index
Mn—number average molecular weight
Mw—weight average molecular weight
PE—polyethylene PD—Mw/Mn RT—room temperature TCE—tetrachloroethane The DSC was measured at a heating rate of 10° C./min, and the melting points were taken as the peak of the melting endotherm on the second heat. $^{13}$C NMR spectra were taken and interpreted generally as described in World Patent Application 9623010. A Varian Unity® 400 MHz or a Bruker 500 125 MHz spectrometer was used, using a 10 mm probe on typically 10–15 weight percent polymer solutions. The MI was taken according to ASTM method 1238, at a temperature of 190° C., using a 2.16 kg weight. Density by IR was determined by melt pressing films 0.2–0.3 mm (8–12 mils) in thickness at 180° C. and cooled at approximately 15° C./min. in the press. The IR spectrum of each film was obtained, and the peak absorbance of the known crystalline band at approx. 1894 cm$^{-1}$ was determined using a two-point baseline employing minima near 2100 and 1850 cm$^{-1}$. The ratio of this absorbance to film thickness (in mils), termed the infrared crystallinity number (IRCN), was related to density by a linear calibration. The method was calibrated by measuring the IRCN and gradient tube densities for melt pressed films of 24 commercial PE resins over a range of densities from 0.88 to 0.96. A linear fit to the data (adjusted r$^2$=0.993) gave the formula: density=6.9707*IRCN+0.8643

EXAMPLE 77

A 600 mL Parr® reactor was cleaned, heated under vacuum and then allowed to cool under nitrogen. In a drybox, to a Hoke® cylinder was added 5 mL toluene and 4.2 mL MAO(13.5 wt % toluene solution). A (0.12 mg in 2 mL toluene) and B (3.5 mg) were mixed with 150 mL 2,2,4-trimethyl pentane in a 300 mL RB flask. The flask was capped with a rubber septa. Both the Hoke® cylinder and the flask were brought out of the drybox. Under nitrogen protection, the catalyst solution was cannulated to the reactor. The reactor was pressured with nitrogen and then the nitrogen pressure was released. The reactor was then pressured with ethylene and the ethylene pressure was released. The reactor was heated to 65° C. and was pressurized with 965 kPa ethylene. The MAO solution was added from the Hoke® cylinder at slightly higher pressure. The ethylene pressure of the reactor was then adjusted to 1.31 MPa. The reaction mixture was allowed to stir for 25 min. The temperature of the reactor was controlled between 87 to 96° C. Heating source was removed. Ethylene was vented to about 210 kPa. The reactor was back filled with 1.38 MPa nitrogen and was vented to 210 kPa. This was done one more time. The reaction mixture was cooled to RT. The reaction mixture was then slowly poured into 400 mL methanol. After stirring at RT for 25 min, the polymer was filtered, blended to small pieces, washed with methanol six times and dried in vacuo. White polymer (24.0 g) was obtained. $^1$HNMR(TCE-d$_2$, 120° C.): 17Me/1000CH$_2$. GPC(PE standard, 135° C.): Mw=72,800; Mn=32,400; PD=2.2. Based on DSC, the polymer had two melting points at 116° C. (14.8 J/g) and 103° C. (108.6 J/g). MI=0.40.

EXAMPLE 78

The supported catalyst was made by stirring a mixture of B (1.0 mg in 1 mL toluene), 54.6 mg 0.1 wt % A in biphenyl, 0.35 g silica supported MAO (18 wt % Al) and 15 mL toluene. After shaking for 30 min, the solid was filtered, washed with 3×5 mL toluene and dried in vacuo for 1 h. It was then stored in a freezer and was used the same day.

A 600 mL Parr® reactor was cleaned and was charged with 150 g of well baked NaCl. It was dried under full vacuum at 120° C. for 2 h. It was then charged with 690 kPa of nitrogen while it was still hot. A water bath was heated to 85° C. In a drybox, 0.66 mL 13.5 wt % MAO-IP toluene solution was mixed with 4 mL of toluene. It was transferred to a 5 mL gas tight syringe. This was brought out of the drybox and the solution was injected into the autoclave under positive nitrogen pressure. The mixture was stirred (600 RPM) at 690 kPa nitrogen for 20 min. Stirring was stopped. The reactor was then charged with 690 kPa of nitrogen. In a drybox, 110 mg of freshly made silica supported catalyst was mixed with 4.5 mL cyclohexane. This was transferred to a 5 mL gas tight syringe. It was brought out of the drybox. The mixture was then injected into the autoclave under positive nitrogen pressure. The mixture was then allowed to stir (600 RPM) at 690 kPa nitrogen for 15 min. Stirring was stopped. Nitrogen was released to 14 kPa. The autoclave was evacuated under full vacuum for 15 min, with stirring the last 5 min. It was recharged with 1.17 MPa nitrogen, then released to 14 kPa, and this was repeated. The mixture was allowed to stir at 500 RPM. Ethylene pressure (2.41 MPa) was applied. The reactor was placed in the 85° C. water bath. The mixture was allowed to stir at 90° C.–97° C. for 2 h. The RT mixture was mixed with 800 mL water. The polymer was filtered, washed with water and was blended into pieces with 400 mL water. It was then filtered, washed with 3×water. The polymer was blended a few more times, followed by water wash. It was then dried in vacuo. White polymer(26.6 g) was obtained. The small amount of leftover alpha-olefins were extracted using a Soxhlet extractor with hexanes. The polymer was then dried in vacuo overnight. Elemental analysis indicated that there was no salt (NaCl) left in the polymer. $^1$HNMR(TCE-d$_2$, 120° C.): 20Me/1000CH$_2$. GPC(PE standard, 135° C.): Mw=92,001; Mn=10,518; PD=8.8. The polymer had a melting point of 126° C. (74 J/g) based on DSC. MI=0.66. The density was 0.919 based on IR.

EXAMPLE 79

The supported catalyst was made by stirring a mixture of B (1.0 mg in 1 mL toluene), 109.2 mg 0.1 wt % A in biphenyl, 0.35 g silica supported MAO (18wt % Al) and 15 mL toluene. After shaking for 30 min, the solid was filtered, washed with 3×5 mL toluene and dried in vacuo for 1 h. It was then stored in a freezer and was used the same day.

A 600 mL Parr® reactor was cleaned and was charged with 150 g of well baked NaCl. It was dried under full vacuum at 120° C. for 2 h. It was then charged with 690 kPa of nitrogen while it was still hot. A water bath was heated to 90° C. In a drybox, 0.50 mL 13.5 wt % PMAO-IP toluene solution was mixed with 4 mL of toluene. It was transferred to a 5 mL gas tight syringe. This was brought out of the drybox and the solution was injected to the autoclave under positive nitrogen pressure. The mixture was stirred (600 RPM) at 690 kPa nitrogen for 20 min. Stirring was stopped. In a drybox, 150 mg of freshly made silica supported catalyst was mixed with 4.5 mL cyclohexane. This was transferred to a 5 mL gas tight syringe. It was brought out of the drybox. The mixture was then injected to the autoclave under positive nitrogen pressure. The mixture was then allowed to stir (600 RPM) at 690 kPa nitrogen for 15 min. Stirring was stopped. Nitrogen was released to 14 kPa. The autoclave was evacuated under full vacuum for 15 min, with stirring the last 5 min. It was recharged with 1.17 MPa nitrogen, then released to 14 kPa, and this was repeated. The mixture was allowed to stir at 500 RPM. Ethylene pressure (2.41 MPa) was applied. The reactor was placed in the 90° C. water bath. The mixture was allowed to stir at 92° C.–95°

C. for 1 h, 56 min. Ethylene was then vented. The polymer/salt mixture was stirred with 600 mL water for 20 min. The polymer was filtered, washed with 3×water. The polymer was blended with 400 mL water, filtered, washed with 3×water, then stirred with 500 mL water for 1 h. This was repeated three times. An AgNO$_3$ test (for Cl) was negative at this point. The polymer was filtered, washed with water and then dried under full vacuum in a 90° C. oil bath overnight. White polymer (58.1 g) was obtained. The small amounts of leftover alpha-olefins were extracted using a Soxhlet extractor with hexanes. The polymer was then dried in vacuo overnight. Elemental analysis indicated that there was no salt (NaCl) left in the polymer. $^1$HNMR(TCE-d$_2$, 120° C.): 19Me/1000CH$_2$. GPC(PE standard, 135° C.): Mw=104,531; Mn=13,746; PD=7.6. The polymer had two melting points at 125° C. (85.8 J/g) and 101° C. (25 J/g) based on DSC. MI=0.96. The density was 0.912 based on IR.

EXAMPLE 80

The supported catalyst was made by stirring a mixture of B (1.0 mg in 1 mL toluene), 54.6 mg 0.1 wt % A in biphenyl, 0.35 g silica supported MAO (18 wt % Al) and 15 mL toluene. After shaking for 30 min, the solid was filtered, washed with 3×5 mL toluene and dried in vacuo for 1 h. It was then stored in a freezer and was used the same day.

A 600 mL Parr® reactor was cleaned and was charged with 150 g of well baked NaCl. It was dried under full vacuum at 120° C. for 2 h. It was then charged with 690 kPa of nitrogen while it was still hot. An oil bath was heated to 85° C. In a drybox, 0.66 mL 13.5 wt % MAO-IP in toluene solution was mixed with 4 mL of toluene. It was transferred to a 5 mL syringe. This was brought out of the drybox and the solution was injected into the autoclave under positive nitrogen pressure. The mixture was stirred (600 RPM) at 690 kPa nitrogen for 20 min. Stirring was stopped. In a drybox, 60 mg of freshly made silica supported catalyst was mixed with 4.5 mL cyclohexane. This was transferred to a 5 mL gas tight syringe. It was brought out of the drybox. The mixture was then injected into the autoclave under positive nitrogen pressure. The mixture was then allowed to stir (600 RPM) at 690 kPa nitrogen for 15 min. Stirring was stopped. Nitrogen was released to 14 kPa. The autoclave was evacuated under full vacuum for 15 minutes, with stirring the last 5 min. It was recharged with 1.17 MPa nitrogen, then released to 14 kPa, and this was repeated once. The mixture was allowed to stir at 500 RPM. Ethylene pressure (2.41 MPa) was applied. The reactor was placed in the 85° C. oil bath. The mixture was allowed to stir at 75° C.–85° C. for 1 h, then at 110° C.–115° C. for 2 hr. Ethylene was vented. The polymer/salt mixture was stirred with 600 mL water for 20 min. Polymer was filtered, and washed with 3×water. The polymer was blended with 400 mL water, filtered, washed with 3×water. The polymer was blended and washed again. It was then dried in vacuo overnight. White polymer (22.7 g) was obtained. $^1$HNMR(TCE-d$_2$, 120° C.): 23Me/1000CH$_2$. GPC (PE standard, 135° C.): Mw=107,173; Mn=25,054; PD=4.3. The polymer had two melting points at 126° C. (32.9 J/g) and 114° C. (50.7 J/g) based on DSC. MI=2.0. The density was 0.919 based on IR.

EXAMPLE 81

The supported catalyst was made by stirring a mixture of B (0.25 mg in 1 mL toluene), 27.2 mg 0.1 wt % A in biphenyl, 0.35 g silica supported MAO (18 wt % Al) and 15 mL toluene. After shaking for 30 min, the solid was filtered, washed with 3×5 mL toluene and dried in vacuo for 1 h. It was then stored in a freezer and was used the same day.

A 600 mL Parr® reactor was cleaned and was charged with 150 g of well baked NaCl. It was dried under full vacuum at 120° C. for 2 h. It was then charged with 690 kPa of nitrogen while it was still hot. A water bath was heated to 85° C. In a drybox, 0.66 mL 13.5 wt % PMAO-IP in toluene solution was mixed with 4 mL of toluene. It was transferred to a 5 mL syringe. This was brought out of the drybox and the solution was injected to the autoclave under positive nitrogen pressure. The mixture was stirred (600 RPM) at 690 kPa nitrogen for 30 min. Stirring was stopped. In a drybox, 200 mg of freshly made silica supported catalyst was mixed with 4.5 mL cyclohexane. This was transferred to a 5 mL gas tight syringe. It was brought out of the drybox. The mixture was then injected to the autoclave under positive nitrogen pressure. The mixture was then allowed to stir (600 RPM) at 690 kPa nitrogen for 15 min. Stirring was stopped. Nitrogen was released to 14 kPa. The autoclave was evacuated under full vacuum for 15 min, with stirring the last 5 min. It was recharged with 1.17 MPa nitrogen, then released to 14 kPa, and this was repeated once. The mixture was allowed to stir at 500 RPM. Ethylene pressure (2.41 kPa) was applied. The reactor was placed in the 85° C. water bath. The mixture was allowed to stir at 85° C.–93° C. for 2 h. Ethylene was then vented. The polymer/salt mixture was stirred with 600 mL water for 20 min. Polymer was filtered, washed with 3×water. The polymer was blended with 400 mL water, filtered, and washed with 3×water. The polymer was blended, filtered and washed again. It was then dried in vacuo overnight. White polymer (12.7 g) was obtained. $^1$HNMR(TCE-d$_2$, 120° C.): 25Me/1000CH$_2$. GPC(PE standard, 135° C.): Mw=116,721; Mn=43,094; PD=2.7. The polymer had two melting points at 122° C. (73.2 J/g) and 91° C. (73.1 J/g) based on DSC. MI=0.42. The density was 0.921 based on IR.

Using data from the GPC and 13C NMR analyses one can calculate a rough K factor for the oligomerization of the ethylene to α-olefin. Based on the Mn, the polymer should have 0.6 ends of chains for each 1000 CH$_2$ groups, so the actual level of Hex+branches in this polymer, excluding ends of chains, is 12.6. Based on 4.4 butyl branches/1000 CH$_2$ groups and 11.5 Hex+branches/1000 CH$_2$ groups, one can calculate that the K constant was about 0.64. As noted above this calculation is subject to several errors and should only be considered approximate.

Table 11 lists the branching distributions of the above prepared polymers, as determined by $^{13}$C NMR. No branches containing odd numbers of carbon atoms were detected. The branching levels for Hex+ include ends-of-chains.

TABLE 11

| Ex. No. | 77 | 78 | 79 | 80 | 81 |
|---|---|---|---|---|---|
| Et* | 6.5 | 5.4 | 6.6 | 4.6 | 4.9 |
| Bu** | 3.2 | 4.1 | 4.1 | 4.0 | 4.4 |
| Hex+*** | 6.5 | 9.2 | 9.7 | 9.6 | 13.2 |
| Hex+/Bu | 2.0 | 2.2 | 2.4 | 2.4 | 3.0 |
| Hex+/Et | 1.0 | 1.7 | 1.5 | 2.1 | 2.7 |

*, , *correspond to 1-butene, 1-hexene, 1-octene and longer olefins, respectively. No odd numbered branches were detected by $^{13}$CNMR

EXAMPLE 82

Rheological measurements were performed on some of the above polymers, as well as two comparative polymers. One of these was DuPont 2020 polyethylene, a low density polyethylene available from E. I. DuPont de Nemours &

Co., Wilmington, De. 19898 U.S.A. The other comparative polymer was a LLDPE, Exceed® 350D60 available from Exxon Chemical., Inc., Houston, Tex., U.S.A., reported to be a copolymer of ethylene and 1-hexene, and to have a density of 0.917 g/cm$^3$. This sample had an Mw of 112,000, as determined by light scattering.

A Bohlin CSM rheometer (Bohlin Instruments, Inc., Cranbury, N.J. 08512 U.S.A.) was used in the parallel plate mode with 25 mm diameter plates and 1 mm gap to make rheological measurements. Each molded sample was bathed in a nitrogen atmosphere and measurements were carried out at 140° C. after briefly heating to 190° C. to remove any traces of crystallinity. Measurements were made in the oscillatory mode between 0.001 and 30 Hz. The maximum stress applied was 2000 Pa and the collected data was always in the linear viscoelastic region. On the same sample, creep/recoil experiments at very low stress (10 Pa) were also performed immediately following the oscillatory flow. Measurements were made over 19 h to determine melt stability via viscosity and elasticity changes.

A special stabilizer package, sample loading and molding procedure were used. Ten ml of a stabilizer solution (0.2g each of Irganox® 1010, Irganox® 1076 and Irgafos® 168 in 100 ml hexane) was squirted onto 1.2 g of pellets. Following air drying, the sample was placed overnight in a vacuum oven at 50° C. with nitrogen bleed. The polymer was then loaded into a cold vacuum mold. Vacuum was applied (pressure no greater than 1.3 kPa absolute) to the mold using a gasket to seal against air contamination. The evacuated mold was heated to 140° C., pressure applied followed by a quench cool to RT. Pressure was released at this point and the sample removed from the mold and placed immediately into the RT rheometer. The sample was then rapidly heated to 190° C. (this took about 5 min) then rapidly cooled (another 10 min) back to the measurement temperature prior to trimming, equilibration at the measurement temperature for about 15 min, and making measurements. The oscillatory flow experiments were performed first; they took about 1.5 h. These were followed immediately by the creep/recoil experiments which took about 16 additional h. Two identical creep/recoil experiments were done with 8 ks and 20,000 ks creep and recoil times, respectively. The entire rheometer was bathed in nitrogen and nitrogen was also applied to the rheometer air bearing. Our experience indicates that small amounts of air contamination with hydrocarbon polymers resulted in sample degradation. Two separate moldings and measurements were made per sample and the results shown are the averaged results shown in FIG. 1. FIG. 1 shows the complex viscosity of the polymers versus frequency of the rheometer, which is a measure of shear, higher frequencies being higher shear rates. Many of the polymers of the Examples above have viscosity profiles similar to the DuPont 2020 LDPE, an excellent processing polymer.

Some of these polymers were also analyzed by SEC (same as GPC) and MALS, multiangle light scattering, and at the same time viscometry, to obtain intrinsic viscosity, Mw, and radius of gyration. The weight averaged molecular weights (Mw) and intrinsic viscosities([η]) were determined using a Wyatt Technology (Santa Barbara, Calif. 93117 U.S.A.) Dawn® DSP light scattering photometer and Viscotek (Houston, Tex. 77060 U.S.A.) 210R viscometer, respectively. Both of these were connected to a liquid chromatograph (Polymer Laboratories, (Amherst, Mass. 01002 U.S.A.) PL210, also called SEC or GPC). Eluent from the SEC is directed to the light scattering instrument through a heated transfer line (also controlled at 150° C.) and then back into the PL210. The oven in the PL210 houses both the differential refractometer and the 210R viscometer as well as the SEC columns. The light scattering instrument employs an Ar ion laser at 488 nm. A single dn/dc of −0.100 (mL/g) (determined from many additional analyses) was used for all calculations. The actual concentration eluting from the column was determined from the calibrated differential refractometer using the dn/dc value of −0.100. In all cases, the integrated concentration was within 2–5% of the weighed mass of polymer injected. The solvent used was 1,2,4-trichlorobenzene; stabilized with 0.05% BHT. A temperature of 150° C. was used for dissolution of solutions and for analysis. Solutions were prepared in small (2 mL) vials at known concentrations of 0.1–0.15%, left in sealed vials in a heating block for 8–12 hours to dissolve, and then analyzed. Polymer solutions were not filtered prior to analysis. Injection volume was 200 microliters, resulting in the injection of 1–1.5 mg for each analysis. Results were obtained using software available from Wyatt Technology. The average intrinsic viscosity, [η], was obtained by taking the ratio of the integrated viscometer peak and the integrated differential refractometer peak. Intrinsic viscosity results and Mw various polymers are shown in Table 12.

The results of the Mw and intrinsic viscosity analyses are also plotted in FIG. 2, along with the results from other polyethylenes and hydrogenated poly(1,3-butadiene) (PB), a linear polymer which is the same (after hydrogenation) as polyethylene. It is clear that at a given Mw, many of the polymers used herein have a lower intrinsic viscosity at a given Mw than linear polyethylene or polyethylenes containing only short chain branching (LLDPE).

TABLE 12

| Polymer | $S_T$ | $P_R$ | Mw | [η] |
|---|---|---|---|---|
| Example 77 | | | 86000 | 1.18 |
| Example 78 | ≧0.61 | 14.4 | 116000 | 1.10 |
| Example 79 | ≧1.8 | 52.6 | 150000 | 1.25 |
| Example 80 | ≧1.6 | 52.1 | 156000 | 1.19 |
| Example 81 | ≧3.8 | 190 | 193000 | 1.38 |
| Exxon Exceed ® 350D60 | 1.00 | 7.95 | 112000 | 1.69 |
| DuPont 2020 LDPE | 0.19 | 69.9 | 278000 | 1.00 |

What is claimed is:

1. A branched polyethylene having fewer than 2 methyl branches per 1000 methylene groups, said fewer than 2 methyl branches excluding end groups, a processability index, $P_R$, of about 40 or more, and (A) a structural index, $S_T$, of about 1.4 or more; or (B) a $S_T$ of less than about 1.4, and one or more feature selected from the group consisting of:
  (i) at least 4 branches each of ethyl and n-hexyl or longer and at least 2 n-butyl branches per 1000 methylene groups;
  (ii) at least 2 branches each of ethyl and n-hexyl or longer and at least one n-butyl per 1000 methylene groups, wherein there are more ethyl branches than butyl branches; and
  (iii) only branches of the formula —(CH$_2$CH$_2$)$_n$H, wherein n is 1 or more.

2. The polyethylene of claim 1, wherein said $P_R$ is about 50 or more.

3. The polyethylene of claim 1, wherein said $P_R$ is about 100 or more.

4. The polyethylene of claim 1, wherein said $S_T$ is about 1.4 or more.

5. The polyethylene of claim 1, wherein said $S_T$ is about 2.0 or more.

6. The polyethylene of claim 1, wherein there are at least 10 branches each of ethyl and n-hexyl or longer and at least 5 n-butyl branches per 1000 methylene groups.

7. The polyethylene of claim 1, wherein said polyethylene has at least two of said features.

8. The polyethylene of claim 1, wherein said polyethylene has all three of said features.

9. The polyethylene of claim 1, which is a homopolyethylene.

10. The polyethylene of claim 8, which is a homopolyethylene.

11. A branched polyethylene which has fewer than 2 methyl branches per 2000 methylene groups, said fewer than 2 methyl branches excluding end groups, at least 2 branches of ethyl and n-hexyl or longer and at least one n-butyl per 1000 methylene groups, wherein there are more ethyl branches than butyl branches, said polyethylene having an intrinsic viscosity in 1,2,4-trichlorbenzene at 150° C. defined by:

$$[\eta] > 0.0007 M_w^{0.63}$$

wherein $M_w$ is the weight average molecular weight.

12. The polyethylene of claim 11, having a structural index, $S_T$, of about 1.4 or more.

13. The polyethylene of claim 12, having an $S_T$ of about 2.0 or more.

14. The polyethylene of claim 11, having a processability index, $P_R$, of about 40 or more.

15. The polyethylene of claim 14, having a $P_R$ of about 50 or more.

16. The polyethylene of claim 15, having a $P_R$ of about 100 or more.

17. The polyethylene of claim 11, having a structural index, $S_T$, of about 1.4 or more, and a processability index, $P_R$, of about 40 or more.

18. The polyethylene of claim 17, having an $S_T$ of about 2.0 or more.

19. The polyethylene of claim 17, having a $P_R$ of about 50 or more.

20. The polyethylene of claim 19, having a $P_R$ of about 100 or more.

21. The polyethylene of claim 11, which is a homopolyethylene.

22. The polyethylene of claim 17, which is a homopolyethylene.

* * * * *